US00PP37172P2

(12) United States Plant Patent
Stringer

(10) Patent No.: US PP37,172 P2
(45) Date of Patent: Dec. 23, 2025

(54) MUSCADINE GRAPE PLANT NAMED 'USDA-ARS-Bertha Mae'

(50) Latin Name: *Vitis rotundifolia*
Varietal Denomination: USDA-ARS-Bertha Mae

(71) Applicant: The United States of America, as represented by The Secretary of Agriculture, Washington, DC (US)

(72) Inventor: Stephen J. Stringer, Poplarville, MS (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 19/170,269

(22) Filed: Apr. 4, 2025

(51) Int. Cl.
*A01H 5/08* (2018.01)
*A01H 6/88* (2018.01)

(52) U.S. Cl.
USPC ..... Plt./207

(58) Field of Classification Search
USPC ..... Plt./206, 207
CPC ..... A01H 5/08; A01H 5/00; A01H 6/88
See application file for complete search history.

(56) References Cited

U.S. PATENT DOCUMENTS

PP7,592 P * 7/1991 Ison ..... Plt./206

OTHER PUBLICATIONS

Our Native Grape, published by C. Mitzky & Co., retrieved on May 7, 2025 at https://www.survivorlibrary.com/library/our_native_grape-grapes_and_their_culture_1893.pdf, 2 cover pages, pp. 104-105. (Year: 1893).*
UPOV Pluto 20250507, retrieved on May 7, 2025 at https://plluto.upov.int/result, one page. (Year: 2025).*
Vitis International Variety Catalogue Passport data, retrieved on May 7, 2025 at https://www.vivc.de/index.php?r=passport%2Fview&id=1195, one page. (Year: 2025).*

* cited by examiner

*Primary Examiner* — June Hwu
(74) *Attorney, Agent, or Firm* — John Fado; Maria Restrepo-Hartwig

(57) ABSTRACT

A new and distinct muscadine grape plant, substantially as herein illustrated and described, characterized by mid-late season ripening berries, typically beginning in mid-August in Mississippi and Texas. 'USDA-ARS-Bertha Mae' has pistillate flowers and requires self-fertile pollinator cultivars to be grown nearby to achieve adequate pollination and fruit set. 'USDA-ARS-Bertha Mae' produces very large (~14 g) berries having sweet and plum-like flavor, a relatively thin skin, and crisp pulp. Berries separate with high percentage of dry stem scars and are highly resistant to rain-induced physiological splitting.

2 Drawing Sheets

Latin name of the genus and species of the plant claimed: 'USDA-ARS-Bertha Mae' is a muscadine grape that is a *Vitis rotundifolia*, Michx.

Variety denomination: The new muscadine grape plant is of the variety denominated 'USDA-ARS-Bertha Mae'.

BACKGROUND OF THE NEW PLANT

The muscadine grape (*Vitis rotundifolia* Michx.) is indigenous to the southeastern United States and has the distinction of being the first cultivated grape in North America. Muscadine grapes have distinctive and pleasant flavors and aromas that make them well suited for fresh fruit and juice, as well as for making pies, preserves, and sweet table wines. In addition to their desirable traits for fresh market and processing, their inherent resistance to pathogens including Pierce's Disease (*Xylella fastidiosa*) and various fungal diseases make them the only grape species that can be profitably grown in much of the southeastern U.S. Currently, commercial farmland devoted to this specialty crop is estimated at 8,000 acres. Although early muscadine grape cultivars were directly selected from wild populations, plant breeders have steadily improved germplasm and developed more productive and higher quality cultivars for over a century.

The nutritional quality of muscadine grapes is excellent, providing a rich source of fiber, essential amino acids, minerals, and vitamins. Recent attention to the nutraceutical properties of muscadine grapes has focused on relatively high concentrations of phytochemicals and antioxidants in skins and seeds including anthocyanins, phenolics, ellagic acid, etc. (Laboratory studies have demonstrated that these compounds have potential medical benefits in humans such as improved cardiovascular health and anti-tumor properties.)

Many older cultivars of muscadine grapes have certain characteristics affecting palatability including thick skins and mucilaginous pulp, berry qualities limiting consumer appreciation for fresh muscadines. However, the development of new cultivars having improved fresh market berry qualities should reduce barriers limiting the consumption and expand awareness of the health benefits of muscadine grapes. Generally, growers of muscadine grapes for the fresh berry market desire berries weighing 10 g or more, having dry stem scars, thin flavorful skins, and crisp pulp, and some consumers may have preferences for berries having bronze or lighter greenish-bronze-colored skins.

SUMMARY OF THE INVENTION

The present invention comprises a new and distinct muscadine grape (*Vitis rotundifolia*, Michx.) plant cultivar jointly released by the USDA ARS and the Mississippi State University which has been given the name 'USDA-ARS-Bertha Mae'. This new variety has been asexually propagated in Poplarville, MS by rooting cuttings under mist in the summer. The following unique combination of traits have been observed in the original plant and in asexually propagated progeny, are firmly fixed, and which in combination distinguish it from existing cultivars:

1) Pistillate flowers
2) Very large berry size with 27 mm diameter and 15 grams) berry weight.
3) Light-green berries.
4) Berries with a firm flesh and crisp skin, and dry stem scars.
5) Berries with a high soluble solids content (Brix°).

The following are the most outstanding and distinguishing characteristics of this new cultivar when grown under normal horticultural practices in Mississippi. 'USDA-ARS-Bertha Mae' differs from most muscadine grape cultivars in that its berries are resistant to rain-induced physiological splitting, have a very large size, light green color, complex fruity and sweet flavor, and relatively non-astringent skins, traits providing enjoyable consumption. The berries have an average weight of ~14 g and most berries ripen in mid to late season (early September in both south MS and east TX). 'USDA-ARS-Bertha Mae' differs from 'Eudora' at least in that the 'USDA-ARS-Bertha Mae' berries are light green, while those of 'Eudora' are purple or black, and the 'USDA-ARS-Bertha Mae' clusters are loose when compared to those of 'Eudora'.

BRIEF DESCRIPTION OF THE FIGURES

The accompanying Figures include color photographs that are as nearly true as it is reasonably possible to make in a color illustration of this type.

DETAILED DESCRIPTION

Figure 1:
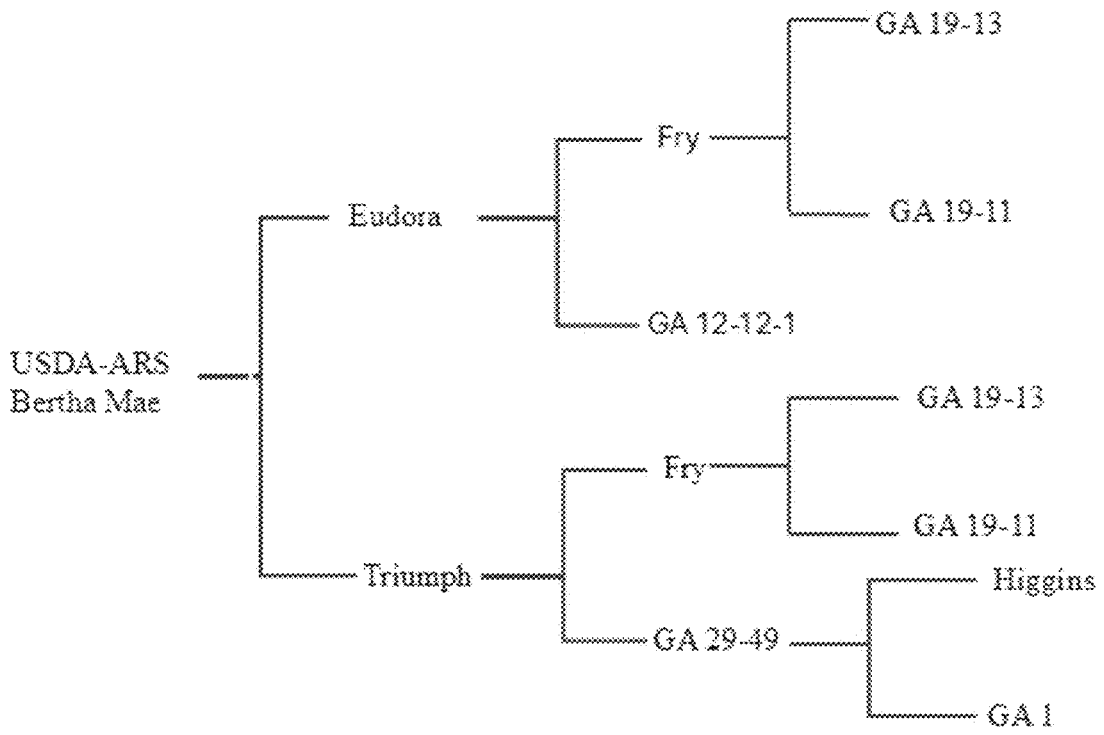
FIG. 1 is a chart showing the pedigree of 'USDA-ARS-Bertha Mae' muscadine grape cultivar.
Figure 2:
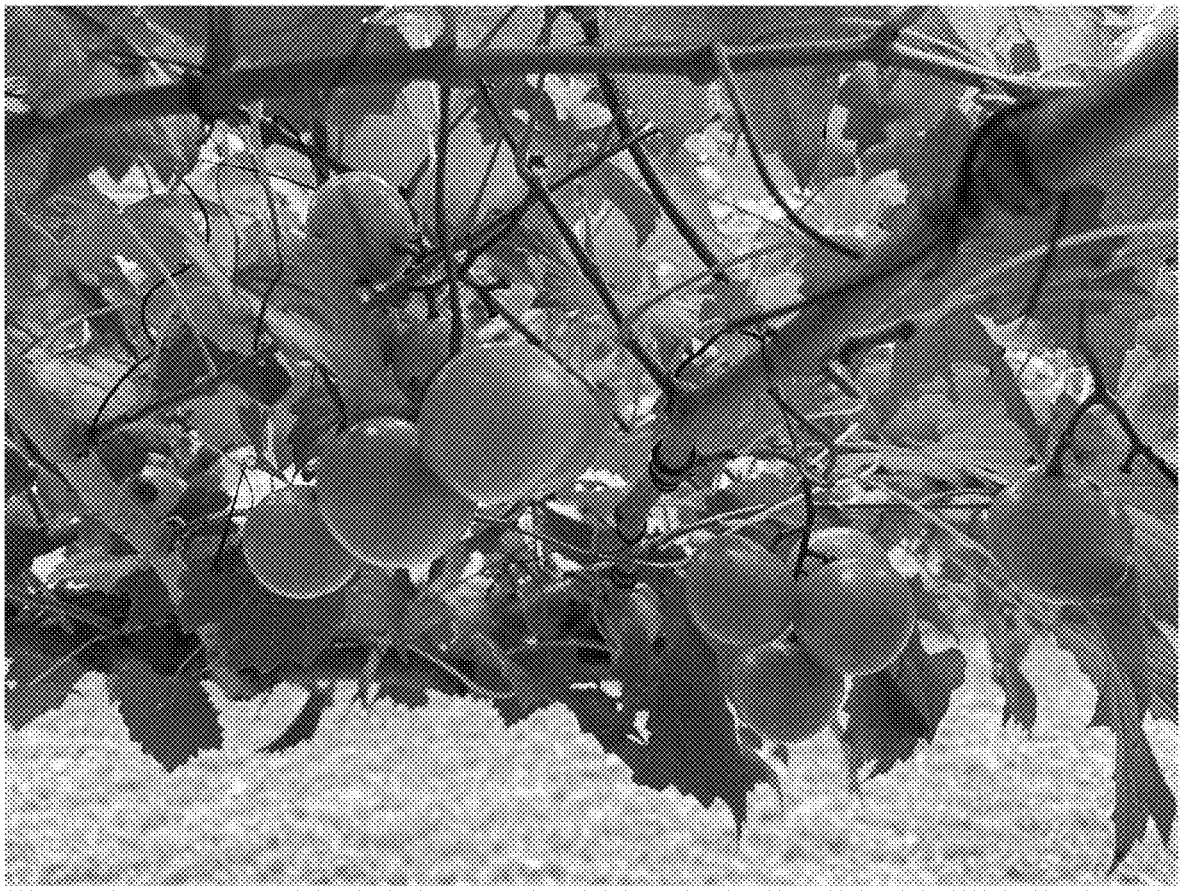
FIG. 2 is a photograph of 'USDA-ARS-Bertha Mae' foliage and berries ripening on mature vines grown at Nacogdoches, TX in August 2023. The colors shown are as true as can be reasonably obtained by conventional photographic procedures.

'USDA-ARS-Bertha Mae', (tested as MS 12-78) is a pistillate cultivar originating from a cross of 'Eudora' (public domain cultivar, USDA ARS, 2010) x 'Triumph' (public domain cultivar, University of Georgia, 1980). FIG. 1 depicts a chart showing the pedigree of 'USDA-ARS-Bertha Mae' muscadine grape cultivar. 'Eudora' was selected as a parent due to its vigorous growth, large berry size, and excellent flavor, and 'Triumph' was selected for its thin skin and crisp pulp and self-fertile flowers. Approximately 100 seedlings from this initial cross were germinated in the greenhouse and planted at McNeill, MS in 2002. 'USDA-ARS-Bertha Mae' was selected by Dr. Stephen Stringer in 2004 and was subsequently asexually propagated via softwood cuttings. 'USDA-ARS-Bertha Mae' was established in replicated field plantings with other selections and muscadine grape cultivars at both McNeill, MS and at Nacogdoches, TX in 2008, and was subsequently evaluated by both Dr, S. J. Stringer and Dr. D. L. Creech at the respective locations.

'USDA-ARS-Bertha Mae' is a mid-late season muscadine with light-green berries and pistillate flowers requiring interplanting among self-fertile cultivars for pollination and fruit set. 'USDA-ARS-Bertha Mae' differs from most muscadine grape cultivars in that its berries are resistant to rain-induced physiological splitting, have a very large size, light green color, and complex fruity and sweet flavor and relatively non-astringent and flavorful skins, traits providing enjoyable consumption. The berries on 'USDA-ARS-Bertha Mae' have an average weight of ~14 g and most berries ripen in mid to late season (early September in both south MS and east TX).

'USDA-ARS-Bertha Mae' has been asexually propagated on many occasions since 2004 by both hard wood and softwood cuttings at Poplarville, MS. It roots readily from softwood cuttings and in all cases the clones propagated from these cuttings have maintained the vegetative and fruit characteristics of the original selection.

'USDA-ARS-Bertha Mae' has been primarily compared with the current larger fruited pistillate cultivars including 'Black Beauty' (U.S. Plant Pat. No. 7,592) and the widely grown 'Summit' (public domain cultivar, University of Georgia, 1977) grown under field conditions both at McNeill, MS and Nacogdoches, TX. Field trials were established to evaluate plant attributes and berry qualities at both, McNeill, MS (lat. 30° 39.6', long-89° 38.8'; plant hardiness zone 9a) in 2006, and Nacogdoches, TX (lat. 31° 60.4, long. −94° 65.6'; USDA plant hardiness zone 8b) in 2010. Plants were grown in four replications on single-wire trellis systems with vine spacings of 20' and 12' within and between rows, respectively, and a trellis wire height of 5'. Standard management practices including periodic drip irrigation as needed, the annual addition of synthetic fertilizers, and winter vine pruning to develop new fruiting wood were employed, however, no insecticides or fungicides were employed at either location.

At the McNeill, MS site, several important plant attributes were measured in 2010, 2012, 2013 and 2014 using subjective ratings based on a scale where the numeric values 1=very poor and 10=very good. This data is shown below in Table 1. Observations on plant vigor (health of trunk, cordons, and overall vegetative growth), productivity (crop), and flavor. Anecdotal observations on plant and berry disease resistance were also made during the berry ripening period. Observations on berry ripening period (% ripe berries) were made in mid-August. At Nacogdoches, TX, subjective ratings of "crop" were made annually (2019-2022). Vines of 'USDA-ARS-Bertha Mae' were as vigorous as 'Summit' and more so than 'Black Beauty' while estimates of yield (Crop) for 'USDA-ARS-Bertha Mae' were slightly greater than that of 'Black Beauty' but less than that of 'Summit'. 'USDA-ARS-Bertha Mae' averaged 7.3 berries per cluster which was comparable to that of 'Summit' but less than 'Black Beauty', and ripening occurred in late August-mid September. Although symptoms of black rot (*Guignardia bidwellii*) were seen on 'USDA-ARS-Bertha Mae' leaves and berries, they were less than that of both 'Summit' and 'Black Beauty'.

TABLE 1

Field Observations at McNeill

| Cultivar | Vigor | Crop | Flavor | Ripeness (%) (August 2024) |
|---|---|---|---|---|
| USDA-ARS-Bertha Mae | 8.0 ± 0.02[z,y] | 7.0 ± 0.7 | 7.8 ± 0.3 | 12.5 ± 2.5 |
| Black Beauty | 7.5 ± 0.3 | 6.8 ± 0.3 | 7.8 ± 0.3 | 12.5 ± 2.5 |
| Summit | 8.0 ± 0.0 | 7.5 ± 0.3 | 7.3 ± 0.3 | 12.5 ± 2.5 |
| Triumph | 7.3 ± 0.3 | 6.8 ± 0.3 | 8.0 ± 0.0 | 27.5 ± 4.8 |

[z]A value of 6 to 7 is considered the minimum acceptable rating for a commercial muscadine grape cultivar.
[y]Values are means ± SE with n = 16.

As seen below in Table 2, laboratory observations on fruit characteristics showed that crop values were comparable to those of 'Black Beauty', but were substantially higher than those of 'Summit'.

TABLE 2

Laboratory Observations on Fruit Characteristics

| Cultivar | Berry Weight (g) | Diameter (mm) | Seeds per Berry | Sugars Brix° (%) |
|---|---|---|---|---|
| USDA-ARS-Bertha Mae | 14.1 ± 0.2[v] | 27.2 ± 0.2 | 3.2 ± 0.1 | 17.6 ± 1.0 |
| Black Beauty | 14.3 ± 0.3 | 28.2 ± 0.1 | 3.4 ± 0.1 | 14.9 ± 0.3 |
| Summit | 9.0 ± 0.4 | 24.4 ± 0.7 | 3.1 ± 0.4 | 17.8 ± 0.7 |
| Triumph | 10.0 ± 0.6 | 24.4 ± 0.2 | 3.6 ± 0.2 | 16.3 ± 0.3 |

| Cultivar | Firmness (g/mm) | Dry Scar (%) | Split Berries |
|---|---|---|---|
| USDA-ARS-Bertha Mae | 241.9 ± 15.4 | 90.4 ± 2.6 | 0.0 ± 0.0 |
| Black Beauty | 327.4 ± 21.6 | 48.8 ± 4.3 | 14.3 ± 6.3 |
| Summit | 263.4 ± 14.2 | 75.0 ± 3.7 | 1.6 ± 0.7 |
| Triumph | 365.4 ± 14.2 | 84.3 ± 3.7 | 0.6 ± 0.7 |

[z]Average weight of 30 berries
[y]Rate (g/mm) at which force required to compress berries increases
[x]Percentage of split berries following 24 h distilled water soaking
[v]Values are means ± SE with n = 16.

Laboratory measurements of fruit qualities were derived from random samples of berries collected from the McNeill, MS trial each year. Measurements included berry weight, diameter, seeds per berry, soluble solids content (Brix°), berry firmness ((rate (g/mm) at which force required to compress berries increases), percentage of dry picking (pedicel) scars, and tendencies for simulated rain-induced physiological splitting. The results are shown below in Table 3. Only berry size and Brix° were measured form berry samples collected from Nacogdoches, TX in 2022. 'USDA-ARS-Bertha Mae's berry size, (weight and diameter) were 14.1 g and 27.2 mm, respectively, size comparable to 'Black Beauty' but larger than 'Eudora', and notably larger than 'Summit'. Number of seeds per berry (3.2) were like that of both cultivars. The firmness measurement of 'USDA-ARS-Bertha Mae' (249.1 g/mm) was comparable to that of 'Summit' but lower than 'Black Beauty'. 'USDA-ARS-Bertha Mae' was also shown to have a very high percentage of dry picking scars (90.4%) and a very low propensity for rain induced physiological splitting (0%), both important attributes for berry shelf-life. The soluble solids content (Brix°) of 'USDA-ARS-Bertha Mae' averaged 17.6%, which was also similar to 'Summit'. Berries from 'USDA-ARS-Bertha Mae' vines collected from the Nacogdoches, TX trials had an average size of 12.2 g which was comparable to that of 'Black Beauty', but greater than 'Summit'. 'USDA-ARS-Bertha Mae's Brix° (17.3%) was slightly above that of both comparison cultivars.

TABLE 3

Field and Laboratory Berry Observations of 2019-2022 Nacogdoches Trials

| Cultivar | Crop | Berry Size (g) | Brix° |
|---|---|---|---|
| USDA-ARS-Bertha Mae | 5.8 ± 1.3[z,y] | 12.2[x] | 17.3[x] |
| Black Beauty | 5.0 ± 0.9 | 13.8 | 16.0 |
| Summit | 2.3 ± 0.5 | 10.7 | 16.0 |
| Triumph | 5.5 ± 1.0 | 4.0 | 15.7 |

[z]Ratings based on subjective scores ranging from 1 to 10, with 1 being the least desirable and 10 being the most desirable.
[y]Values are means ± SE with n = 4 (2019-2022)
[x]2021 values n = 1

PLANT CHARACTERISTICS

In the following description, color references are made to The Royal Horticultural Society Colour Chart, copyright 1966, except where general terms of ordinary dictionary significance are used. The description is of a six-year-old 'USDA-ARS-Bertha Mae' plant.

Vines: 'USDA-ARS-Bertha Mae' vines grow moderately, i.e. growth of mature lateral canes in McNeill, MS are 1.0 to 2.2 m in length per growing season and are greyed-orange in color (RHS 165A). Trunk bark color is greyed-orange (RHS 177D) and rough in texture, and has a girth of 7-9 cm at 0.75 m above the soil line. Shoot tips are also greyed-orange in color (RHS 174B). Internode lengths are 5 to 6 cm in length. Tendrils are 8 to 10 cm long, unbranched, and discontinuous along the nodes. Tendril color is orange-red (RHS 35A).

Foliage: Leaves average about 9 cm in length and 8 cm in width. The leaves are circular with widely toothed margins and are glabrous on both upper and lower surfaces. Mature upper leaf surfaces are dark green (RHS 136A) and somewhat shiny, while the lower surfaces are light green (RHS 138A) and less shiny than the upper surface. The petiole length equals or slightly exceeds the blade midrib, and the petiole sinus is open.

Flowers: The flowers are pistillate-not self-pollinating. Flowers are small, unopened flowers at blooming average 2.5 mm in diameter and 2.0 mm ovary diameters in open flowers. The flowers are indiscrete, yellow green (RHS 138C), and are born in racemose panicles opposite leaves at the base of current seasons growth. The anthers are non-functional and are light yellow (RHS 21D) and are supported by defective filaments at the base of the ovary. Flowers are short-lived, lasting approximately 3 to 4 days and 'USDA-ARS-Bertha Mae's' flowers typically bloom from Mid to late May at McNeill, MS.

Fruit: The vines produce large light-green fruit (RHS 152D) that ripen in a two-week period from late August through early September at McNeill, MS. As seen in Table 3, the berries are large and round with a diameters of 27 mm and weight of 14 g, and contain 18% soluble solids with 3.2 seeds per berry. Seeds are grey-brown (RHS 152B) at maturity. The berries separate from the pedicel with a relatively dry stem scar, i.e. less than 10% of berries are torn at the point of detachment from the pedicel and are highly resistant to rain-induced physiological splitting.

Other characteristics of 'USDA-ARS-Bertha Mae' are as follow. The time of bud burst is medium. The amount of anthocyanin coloration on prostrate hairs of the young shoot tip are very sparse. The shoot color on the ventral side of the internodes is green and red. The young leaf upper surface color is moderate yellow-green (RHS 146B). The amount of prostrate hairs on the lower leaf surface between main veins on young leaves is very sparse. The color of the shoot on the ventral side of internodes is green red. The number of leaf lobes is 22, the leaf teeth are short, and both sides of the leaf are straight. The amount of anthocyanin on the upper surface of the mature leaf main vein is very low. Prostrate hairs on the lower side of the mature leaf main veins are absent. Erect hairs between the veins on the lower side of the mature leaf are absent. The amount of openness of the petiole sinus based on the UPOV International Union for the Protection of New Varieties of Plant Grapevine TG/50/9 2008 is 2, wide open.

The midrib color is orange red (RHS 35A). The midrib length is about 55 mm, similar to that of the petiole length, which is about 53 mm. There is an average of about 7.6 berries per cluster, with a medium bunch density, and the average bunch size is medium. The average berry cluster weight is approximately 110 g. The length of the bunch peduncle is short, The flesh color of the berries is light green. Pollinator cultivars needed for pollination and fruit set of 'USDA-ARS-Bertha Mae' may be any one of 'CARLOS', 'ISON', 'HALL', 'NOBLE', or 'TRIUMPH'.

'USDA-ARS-Bertha Mae' holds up very well in cold storage, and is suitable for the Fresh Market. 'USDA-ARS-Bertha Mae' thrives in USDA plant hardiness zones 8 and 9. 'USDA-ARS-Bertha Mae' is very heat resistant, and relatively cold hardy.

I claim:

1. A new and distinct variety of muscadine grape plant named 'USDA-ARS-Bertha Mae' substantially as illustrated and described herein.

* * * * *